United States Patent
Weyh et al.

(10) Patent No.: US 11,666,774 B2
(45) Date of Patent: *Jun. 6, 2023

(54) PULSE SOURCE AND METHOD FOR MAGNETICALLY INDUCTIVE NERVE STIMULATION

(71) Applicant: Universitat der Bundeswehr Munchen, Neubiberg (DE)

(72) Inventors: Thomas Weyh, Neubiberg (DE); Florian Helling, Neubiberg (DE)

(73) Assignee: Universität der Bundeswehr München, Neubiberg (DE)

( * ) Notice: Subject to any disclaimer, the term of this patent is extended or adjusted under 35 U.S.C. 154(b) by 684 days.

This patent is subject to a terminal disclaimer.

(21) Appl. No.: 16/498,267

(22) PCT Filed: Apr. 13, 2018

(86) PCT No.: PCT/EP2018/059569
§ 371 (c)(1),
(2) Date: Sep. 26, 2019

(87) PCT Pub. No.: WO2018/189387
PCT Pub. Date: Oct. 18, 2018

(65) Prior Publication Data
US 2020/0030622 A1    Jan. 30, 2020

(30) Foreign Application Priority Data
Apr. 13, 2017   (DE) .......................... 102017108084.8

(51) Int. Cl.
*A61N 2/00*      (2006.01)
*A61N 1/40*      (2006.01)
*A61N 2/02*      (2006.01)

(52) U.S. Cl.
CPC ............. *A61N 2/006* (2013.01); *A61N 1/40* (2013.01); *A61N 2/02* (2013.01)

(58) Field of Classification Search
CPC ............. A61N 2/006; A61N 1/40; A61N 2/02
See application file for complete search history.

(56) References Cited

U.S. PATENT DOCUMENTS 9,496,799 B2 * 11/2016 Goetz .................. H02M 3/158
11,056,982 B2 * 7/2021 Weyh .................. H02M 7/4835
(Continued)

FOREIGN PATENT DOCUMENTS

DE     102009023855 A1 * 12/2010 ............... A61N 2/02
DE     102010004307 A1    7/2011
(Continued)

OTHER PUBLICATIONS

L.A. Silva, S. P. Pimentel and J. A. Pomilio, "Analysis and Proposal of Capacitor Voltage Control for an Asymmetric Cascaded Inverter," 2005 IEEE 36th Power Electronics Specialists Conference, Recife, Feb. 2005, pp. 809-815.
(Continued)

*Primary Examiner* — Catherine M Voorhees
(74) *Attorney, Agent, or Firm* — Fletcher Yoder, P.C.

(57) ABSTRACT

The invention relates to a modular pulse source consisting of a main module and at least one additional module which are connected in series to each other in the sense of two-terminal circuits. The modules each comprise an energy storage device. The energy storage device of the main module is initially charged by a charging circuit. A stimulation coil is connected at the two ends of the series connection and as a result of a voltage pulse delivered by the chain of modules generates a magnetic field which in turn causes an induced electrical pulse or a respective electric field.

20 Claims, 11 Drawing Sheets

(56) References Cited

U.S. PATENT DOCUMENTS

| | | | |
|---|---|---|---|
| 2011/0013441 A1* | 1/2011 | Gruber | H02M 1/36 323/311 |
| 2013/0030239 A1* | 1/2013 | Weyh | A61N 2/006 600/14 |
| 2013/0200860 A1* | 8/2013 | Takeda | H02M 3/07 320/167 |
| 2014/0049230 A1* | 2/2014 | Weyh | H02M 7/483 323/207 |
| 2021/0111642 A1 | 4/2021 | Weyh et al. | |

FOREIGN PATENT DOCUMENTS

| | | | | |
|---|---|---|---|---|
| DE | 102014008820 A1 | 12/2015 | | |
| DE | 102014110410 A1 | 1/2016 | | |
| WO | 2010135425 A1 | 11/2010 | | |
| WO | 2010139376 A1 | 12/2010 | | |
| WO | WO-2010139376 A1 * | 12/2010 | | A61N 2/02 |
| WO | 2011083097 A1 | 7/2011 | | |

OTHER PUBLICATIONS

S. Laali, K. Abbaszadeh and H. Lesani, "A new algorithm to determine the magnitudes of dc voltage sources in asymmetric cascaded multilevel converters capable of using charge balance control methods," 2010 International Conference on Electrical Machines and Systems, Incheon, Nov. 2010, pp. 56-61.

S. Mariethoz, "Design and control of high performance modular hybrid asymmetrical cascade multilevel inverters with active voltage balance and low losses," 2012 IEEE Energy Conversion Congress and Exposition (ECCE), Raleigh, NC, Sep. 2012, pp. 2513-2520.

J. Pereda and J. Dixon, "Cascaded Multilevel Converters: Optimal Asymmetries and Floating Capacitor Control," in IEEE Transactions on Industrial Electronics, vol. 60, No. 11, Nov. 2013, pp. 4784-4793.

Z. Du, L. M. Tolbert, J. N. Chiasson, B. Ozpineci, H. Li and A. Q. Huang, "Hybrid cascaded H-bridges multilevel motor drive control for electric vehicles," 2006 37th IEEE Power Electronics Specialists Conference, Jeju, Jul. 2006, pp. 1-7.

J. Dixon and L. Moran, "High-level multistep inverter optimization using a minimum number of power transistors," in IEEE Transactions on Power Electronics, vol. 21, No. 2, Mar. 2006, pp. 330-337.

Notification of Prior Art for DE Application No. 102017108084.8 dated Mar. 18, 2021, pp. 1-4.

International Search Report for PCT/EP2018/059569 dated Jun. 21, 2018, 4 pages.

Office Action for DE Application No. 102017108084.8 dated Jan. 3, 2018, 8 pages.

* cited by examiner

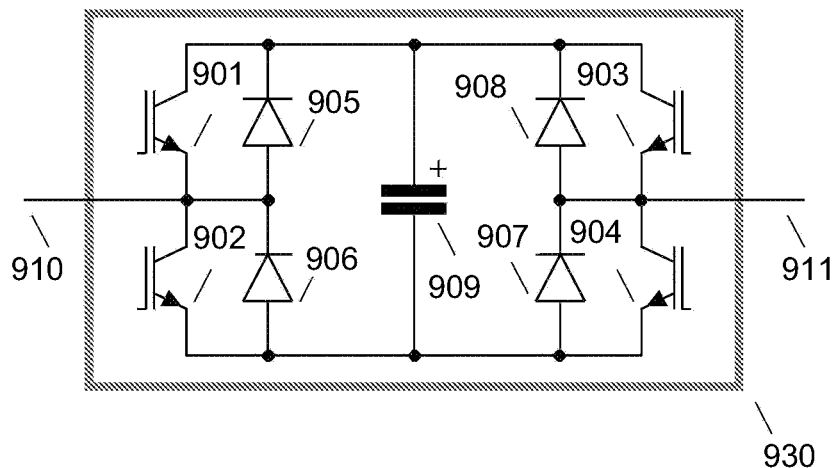
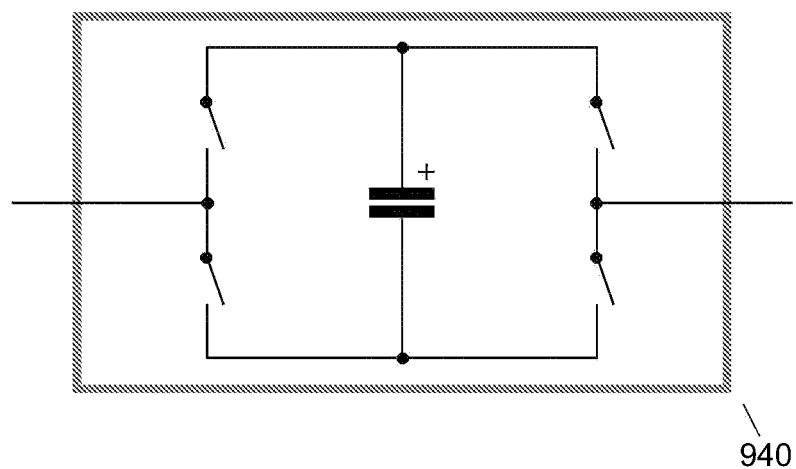
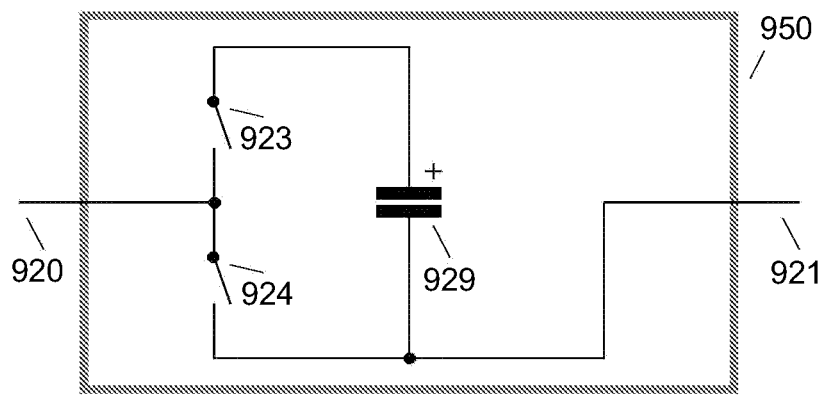
Fig. 9

PULSE SOURCE AND METHOD FOR MAGNETICALLY INDUCTIVE NERVE STIMULATION

CROSS-REFERENCE TO RELATED APPLICATIONS

This application is a national stage of PCT application no. PCT/EP2018/059569, entitled "PULSE SOURSE AND METHOD FOR MAGNETICALLY INDUCTIVE NERVE STIMULUS", filed on Apr. 13, 2018, which claims priority to German application no. DE102017108084.8 filed on Apr. 13, 2017, both of which are hereby incorporated by reference in their entirety.

The present invention relates generally to a method and devices for stimulating nerve and muscle cells in the body tissue in accordance with the magnetic induction principle by brief, strong magnetic field pulses that are generated by a coil and a respective pulse source. The invention further relates to electrical power circuits for generating freely selectable temporal courses of brief, strong current pulses through the coil in order to generate pulse-shaped magnetic fields for stimulating nerve and muscle cells.

BACKGROUND OF THE INVENTION

Generally, specific cells in the body tissue can be stimulated by electric fields acting from the outside. Nerve or muscle cells can be excited, in particular, by depolarization of an axon or a bundle of fibers, respectively, stimulated by an external field, and the triggering of action potentials and the subsequent stimulus conduction resulting therefrom. This is achieved in that the electric fields cause electrical currents in the tissue, which in turn trigger action potentials in these cells. This type of triggering action potentials by an electric field acting directly upon the axon is a non-physiological process: In nature, action potentials are generated in the cell body of the nerve cell itself, after signals coming in via the dendrites have been linked respectively.

The externally acting electric field must meet certain conditions in order to trigger such a potential for action with regard to the course of time. Furthermore, a certain minimum strength must also be obtained. In particular, regarding the triggering of an action potential, different cell types also react differently to temporal courses and strengths of the fields acting from the outside. By way of example, sensory nerve fibers, that are also responsible for the transmission of pain signals, due to their smaller diameter require a higher electrical field strength for depolarization (i.e. for triggering an action potential) than motor nerve fibers. At moderate stimulus intensities, it is therefore possible to stimulate only the motor but not the sensory fibers and therefore to stimulate nerves virtually without pain.

The principle of magnetic induction can be used in particular for this type of stimulation. In this, a time-varying magnetic field generates an induced electric field. The time-varying magnetic field can be generated by a coil which has time-varying current passing through. This coil is located, for example, on the skin above the nerve tissue to be stimulated, so that the magnetic field generated can penetrate the tissue and, according to the induction principle, generate the currents in the tissue necessary for stimulation. The stimulation by so-called inductive magnetic stimulation can there occur contactless, since the magnetic field can penetrate body tissue without obstruction. The time-dependent magnetic fields are generated by brief current pulses having a duration of usually of 50-400 microseconds. The principle of inductive stimulation is in principle based on a temporal change of the magnetic field, since electric fields can be induced only in this way by the coil in the tissue. For this reason, only time-varying electric fields can be created in the tissue. For example, no efficient simple monophasic rectangular pulses having a direct (DC) component can therefore be generated as they are used in the electrical stimulation.

One advantage of the inductive magnetic stimulation is that it is contactless, since the magnetic field of the coil also reaches the body tissue that is disposed at a certain distance from the coil. Therefore, nerve cells can be stimulated also in a sterile manner. Another advantage is, that the method in contrast to electrical stimulation via electrodes is almost completely painless, because contrary to electrical stimulation, no high current densities, which irritate the respective skin sensors during electrical stimulation and cause a sensation of pain, can arise at the locations of application of the electrodes. For these reasons, the method is also particularly suitable for stimulation of deeper-lying tissue structures (e.g. the cerebral cortex through the cranial bone) and for pain-free muscle stimulation e.g. in the field of rehabilitation.

Due to these advantages, the inductive magnetic stimulation was able to already prevail over electric stimulation in some fields or even to open up new fields of application. The procedure is very common for application to the central and the peripheral nervous system.

Currently it is the only non-invasive procedure with which, for example, certain brain regions can be selectively activated without any pain for the individual (i.e. triggering nerve action potentials or subliminal influencing of nerve cells in these regions) such that responses by nerve cells can be processed by the body just like, or at least very similar to, naturally occurring nerve impulses.

The inductive magnetic stimulation is used in fundamental research as a tool for common examination together with functional magnetic resonance imaging. Selective excitation (and inhibition) of certain brain regions can be induced via pulses, the effects of which can in turn be examined by magnetic resonance imaging.

One field of application is so-called cortical mapping, in which functional assignments of the motor cortex are carried out via very precise inductive stimuli on the cerebral cortex (through the intact cranium). Preoperative planning for brain tumor operations can be significantly improved in this way.

Furthermore, there are applications of inductive magnetic stimulation regarding peripheral motor nerves. In this respect, repetitive continuous stimulation with fast pulse sequences (approx. 10 to 50 pulses per second) is of great significance as this can create continuous muscle contractions, the strength of which can be controlled by the intensity of the stimulation pulses. Applications for apparatuses used in competitive sports are additionally known.

FIG. 1 shows a typical arrangement of the previous use of the inductive magnetic stimulation. Pulse source 110 generates a brief strong current pulse and conducts it to coil 120. Coil 120 is positioned close to the body nerve tissue to be stimulated, so that the magnetic field generated can penetrate through this tissue structure. The magnetic field generated by the coil induces an electric field in the body tissue, presently upper arm 130, which stimulates nerve and muscle tissue by way of the resulting currents.

However, for the inductive magnetic stimulation, this detour through the magnetic field of the coil also causes important technical problems:

The required magnetic flux densities are in the range of about 1 Tesla, so that during the very brief magnetic stimulation pulse, extremely high electric power must be provided to the coil in order to generate the appropriate field energies. The required electrical power can reach values of several megawatts and the currents can reach several kiloamperes at voltages of several kilovolts. Therefore, the pulse sources are technically complex; furthermore the coil very quickly overheats due to the current heat losses, where it must presently be additionally considered that the coil may not reach too high temperatures as it is a component that can directly contact the body.

In order to nevertheless be able to provide respective currents and energies for this type of stimulation with a reasonable technical available effort, magnetic stimulation devices presently operate according to the principle of the resonant oscillating circuit in which a capacitor discharges its energy into the coil. The principle of generating powerful pulses for the coil is therefore based on a continuous charge of the oscillating circuit capacitor by way of a charging device at relatively low power and the rapid discharge of the energy content of this capacitor to the coil for generating the brief strong magnetic field pulse.

FIG. 2 shows the basic circuit structure of an inductive stimulation device as used in the first devices, in particular for contactless stimulation of cortical nerve structures through the intact cranial bone (R. Siebner, U. Ziemann, "Das TMS-Buch", Springer publishing house, ISBN-13 978-3-540-71904-5). For this purpose, the circuit uses a powerful damped electrical oscillation circuit (resonator) comprising a capacitor 220, a damping resistor 230, a diode 240, a thyristor 250 and coil 260. Charging circuit 210 charges capacitor 220 to a voltage of several thousand volts. The energy content of the capacitor amounts to several 100 joules. Thyristor 250 serves as a switch which during ignition connects capacitor 220 with magnetic coil 260 and thus lets the current flow into the coil begin.

FIG. 3 shows the temporal course of current and voltage in the coil according to the circuit of FIG. 2. Upon ignition of the thyristor, an initially sinusoidally increasing current flow develops, which generates a corresponding magnetic field increasing with time. This magnetic field in turn induces ring currents in the body tissues as a result of its change over time. The phase-shifted coil voltage has its first zero crossover exactly upon reaching the current peak value. Since from this point on, the coil voltage reverses its sign, the damping circuit comprising resistor 230 and diode 240 now becomes active, preventing further oscillation of the oscillation circuit. Therefore, the coil current, after reaching its peak value, slowly drops back to zero. The typical time period between the thyristor ignition and reaching the current peak value is about 50 to 150 microseconds. However, the entire pulse energy of the capacitor in resistor 230 and in the coil conductors of the coil is transformed to heat by this damping circuit.

This damping circuit being employed in the first devices, which dampens the oscillation from the first dropping current edge (after one quarter of the period duration), characterizes the so-called monophasic stimulation, as the coil current during the pulse only flows in one direction, i.e., does not change its sign. Since the pulse energy of the magnetic field in these devices is completely lost with each pulse, these devices have particularly high energy consumption.

These first devices were therefore not suitable for so-called repetitive stimulation for which 10 to 50 pulses per second are required. Furthermore, also the size of the devices and their high price make it difficult to tap new fields of application.

One important development goal regarding the devices for inductive magnetic stimulation lies in the reduction of energy consumption and heat development in the coil (R. Siebner, U. Ziemann, "Das TMS-Buch", Springer publishing house, ISBN-13 978-3-540-71904-5). It was shown by experimental studies, that an undamped sinusoidal temporal course of the coil current and thus also of the magnetic field at the same amplitude shows an equivalent effect regarding nerve stimulation as the current curve of FIG. 3.

FIG. 4 shows a further basic circuit topology for stimulation devices, as it is used in newer device generations. This device generates sinusoidal current or field pulses, respectively. Here as well, charging circuit 210 charges capacitor 220 to a voltage of several thousand volts. Thyristor 410 again serves as a switch which during ignition connects capacitor 220 with magnetic coil 260. In contrast to the monophasic stimulator circuit of FIG. 2, however, no damping circuit is used for this circuit, so that the oscillating circuit continues to oscillate even after the first zero crossover of the coil current.

FIG. 5 shows the temporal course of the current and the voltage in the coil according to the circuit of FIG. 4. Upon igniting the thyristor, a sinusoidally increasing current flow develops, which generates a corresponding magnetic field increasing with time. After half a sinusoidal oscillation, at the point in time T/2, the current in the oscillating circuit changes its polarization. At this point in time, diode 420 takes over conduction of the coil current until a full sinusoidal oscillation at point in time T is reached. A renewed reversal of the current direction and thus continued oscillation is prevented because thyristor 410 at this point in time T is no longer conductive. Due to the reversal of the direction of current during a pulse at point in time T/2, this type of stimulation is generally referred to as biphasic magnetic stimulation.

It can be achieved by the circuit principle according to FIG. 4 that a large proportion of the field energy expended for coil 260 can be returned to capacitor 220 thus reducing the losses in both the pulse source as well as in coil 260. The losses of the circuit of FIG. 4 mainly result via the ohmic resistances of the circuit components involved and their connection cables.

However, since the current amplitude required for successful stimulation remains approximately unchanged compared with the devices with a monophasic pulse shape, the necessary voltage and the energy content of capacitor 220 remain nearly the same as with monophasic devices.

FIG. 6 shows a variation of the circuit topology of FIG. 4 as it is likewise used in newer devices (R. Siebner, U. Ziemann, "Das TMS-Buch", Springer publishing house, ISBN-13 978-3-540-71904-5). Here as well, charging circuit 210 charges capacitor 220 to a voltage of several thousand volts. Thyristor 610 serves as a first switch which during ignition connects capacitor 220 with magnetic coil 260. The current through the coil or thyristor 610 reaches a zero crossover of the current for the first time after a quarterly sine wave If there is no control signal applied to the thyristors at this time, the oscillating circuit then stops; the capacitor is negatively charged at this point in time. The energy stored in the capacitor corresponds almost to the energy at the start time of the pulse and is reduced only by the respective losses of the circuit. Now second thyristor 620 can be ignited and thereby generate a pulse with an inverse voltage curve as compared to the first pulse. In particular, the duration between two such pulses can be selected almost arbitrarily short, since no recovery times of the thyristors must be observed due to the distribution of the two pulses on two thyristors.

FIG. 7 shows the temporal course of current and voltage in the coil according to the circuit of FIG. 6. Upon igniting the thyristor, a sinusoidally increasing current flow develops which generates a corresponding magnetic field increasing over time. After half a sinusoidal oscillation, at time T/2, the current in the oscillating circuit reaches its first zero point. If second thyristor 620 is not ignited at this point in time, then reversal of the current direction is not possible, so that a continued oscillation is prevented already after a half-wave. Ignition of the thyristor 620 at a later time generates a further half-wave pulse in the coil with reversed current and magnetic field direction. Alternatively, however, upon reaching the first current zero point, second thyristor 620 can also be ignited directly so that a full sinusoidal oscillation is formed, similar to FIG. 5. In any case, the field energy of the coil is to a large extent returned to the capacitor also with this circuit.

Depending on the choice of the end time of the pulse, a distinction is therefore made regarding the pulse shape of the inductive stimulation devices according to FIG. 4 between biphasic full-wave stimulation (duration of the current pulse one full sine period) and biphasic half-wave stimulation. It is disadvantageous with the biphasic half-wave stimulation, however, that after the pulse, the voltage direction in the capacitor is inverted as compared to the state prior to the pulse discharge, making the respective charging circuit more complex. Furthermore, the direction of the magnetic field in the biphasic half-wave stimulation also changes, so that successive pulses create slightly different effects in the tissue.

The energy recovery in accordance with the circuits of FIG. 4 and FIG. 6 allows a reduction of the energy lost with each pulse and thus also of the power heat losses in the coil and the power electronics. This also allows the construction of repetitive inductive stimulation devices which can deliver up to 100 pulses per second. However, energy consumption and coil heating is still considerable, especially for this repetitive operation. In particular coil heating results from the very high coil currents required that are in the kiloampere range.

Another way to reduce energy losses can be achieved by reducing current heat losses of the coil (R. Siebner, U. Ziemann, "Das TMS-Buch", Springer publishing house, ISBN-13 978-3-540-71904-5). This is done by increasing the effective conductor cross-section, in that, firstly, thicker conductor material can be used and, secondly, the conductor can be filamented by using high-frequency wire, so that the current displacement effects in the conductor are reduced. However, the electrical resistance of the coil cannot be reduced arbitrarily for weight reasons.

As to the temporal course of the stimulation pulse, the three wave types mentioned, the damped monophasic pulse, the biphasic half-wave pulse and the biphasic full-wave pulse, still represent the only pulse shapes that are used in commercially available inductive magnetic stimulation devices. All these wave shapes are ultimately based on the principle of the resonant oscillating circuit, where the coil is the inductor.

Therefore, the previously used devices also have the great disadvantage that the pulse duration depends on the inductance of the coil. In particular, for example, small coils often have design-related lower inductance than large coils; therefore, the pulse duration with previous systems could not be kept constant in an optimal range when using different coils.

Occasional experiments with other pulse shapes, as in Peterchev et al. 2008 with a rectangular shape (A. V. Peterchev, R. Jalinous, and S. H. Lisanby: "A Transcranial Magnetic Stimulator Inducing Near-Rectangular Pulses With Controllable Pulse Width" (cTMS), "IEEE Transactions on Biomedical Engineering", vol. 55, no. 1, 2008) are either very energy inefficient or they lead to highly complex technical structures and are therefore too expensive for commercial technical realization.

For all applications, the disadvantage of inductive magnetic stimulation still is therefore high energy consumption, very rapid overheating of the coil, and large weight of the charging and pulse generating electronics.

Another disadvantage is that the temporal course of the stimulus pulse cannot be individually flexibly adapted to certain nerve cell or axon types or other requirements. The existing stimulation devices can therefore not selectively target specific cell types, nor can they allow conclusions to be drawn about cell type or disease by way of the differently applied pulse shapes.

OVERVIEW OF THE INVENTION

It is the object of the invention to provide a device and a method for generating finely stepped voltage and current curves for generating optimized electrical pulses with the aid of which the aforementioned drawbacks are avoided, where the pulses causes the stimulation of nerve and/or muscle cells using a stimulation coil.

This object is satisfied, in particular, with a device according to claim 1 and a method according to the independent claims. Advantageous embodiments of the invention are the respective object of the dependent claims.

According to one aspect of the invention, a modular pulse source is proposed, consisting of a main module and at least one, preferably several additional modules, which are all connected in series to each other in the sense of two-terminal circuits. The modules each comprise an energy storage device, preferably formed by a capacitor. The energy storage device of the main module is initially charged by a charging circuit. A stimulation coil is connected at the two end points of the series connection and, as a result of a voltage pulse delivered by the chain of modules, generates a magnetic field which in turn causes and induced electrical pulse or a respective electrical field. The modules are preferably configured as two-quadrant modules or four-quadrant modules. These switching devices of the modules are controlled by a controller device. In addition to an active operation in which the voltage of the respective storage device contributes to the voltage path of the series connection, the modules preferably have a bypass operation in which the module is electrically bridged and does not contribute to the voltage path and preferably, an inverted operation, in which the voltage contribution acts inverted upon the voltage path. The controller device preferably controls the voltage contributions acting in the active state such that they differ from each other according to the powers of two. It is then possible to generate a large number of voltage steps with a relatively small number of modules which then act upon the stimulation coil coupled and thereby effect the desired voltage curve over time. The invention is based, on the one hand, on the realization that with improved adaptation of the temporal course of the fields and currents induced in the tissue to the dynamic charge transport phenomena of the nerve or muscle fibers, the required field strength and field energy for inductive stimulation of these fibers can be reduced.

The invention is further based on the realization that, by appropriately controlling the configurations of the modules, a finely stepped voltage curve of a pulse can be generated at the ends of the series connection by way of a series connection of several double-pole modules, each containing one or more energy storage elements (such as a capacitor). Accordingly, a stimulation coil for inductive nerve stimulation can be connected to the ends of the series connection in order to generate pulses with a freely configurable profile of the induced field strength.

The double-pole modules can preferably be configured as four-quadrant modules. Each module can then switch the voltage of the energy storage element positive or negative at its two terminals, regardless of the current direction. Furthermore, these modules can assume a bypass state in which the module electrically connects its two terminals directly to each other, where the energy storage neither delivers nor takes up charge. Furthermore, the series connection contains at least one main module which likewise contain at least one energy storage element each. This main module can also be configured as a four-quadrant or a two-quadrant module. In the latter case, the module can only switch the states bypass or positive voltage at the terminals. The main module contains an energy storage element which can preferably store at least the energy for the pulse to be delivered. Furthermore, this main module is supplied by a charging circuit in order to charge the required energy into the energy storage element. The storage capacities of the energy storage elements of the other four-quadrant modules can be much smaller because these energy storage elements can be discharged or charged by the current of the entire series connection during the pulse output. However, the energy storage elements of the other four-quadrant modules can likewise be precharged by a charging circuit before the pulse is delivered. During the pulse delivery itself, however, no noteworthy charge of the main module or the other four-quadrant modules takes place.

The voltages of the energy storage elements of the individual modules exhibit different values, so that a series connection of individual modules enables a very finely stepped adjustment of the desired voltage curve during the pulse delivery by way of appropriately activating, disabling and reversing the polarity of the energy storage elements Preferably, stepping down the individual voltages of the energy storage elements of the modules by the power of two is possible, but also by other steps. The energy storage element of the supplied main module represents the highest voltage step.

Depending on the current through the series connection of modules, the energy storage elements of each module take up charge during a pulse according to their instantaneously switched state, deliver charge or maintain their instantaneous state of charge (bypass state). The respectively selected step-down of the voltages of the modules makes it possible that at least two module configurations always exist for each voltage step to be output, so that the energy storage elements of the respective modules—except for the energy storage element of the main module—can be either charged or discharged.

This allows a pulse source to be set up from a series connection of individual modules. If the energy storage element of the main module is charged to the target voltage and the energy storage elements of the further four-quadrant modules are preferably also charged to their target voltages, then a desired voltage curve can be created in fine steps by a temporal sequence of module configurations. For every module configuration, each individual module of the series connection is respectively switched on, has its polarity reversed, or is switched off. Since the states of charge (and therefore also the voltages) of the energy storage elements change during the delivery of a pulse due to the associated coil current, the configuration of the modules is constantly changed in short sequences during the pulse, so that module capacitors with too low a voltage are recharged and module capacitors with too high a voltage can be discharged.

BRIEF DESCRIPTION OF THE DRAWINGS

The above-mentioned and other objects, features, and advantages of the present invention will become more apparent from the following detailed description in combination with the accompanying drawings, in which:

FIG. 9 shows the possible structure of a four-quadrant module and a two-quadrant module, as it can be used in the present invention;

In the drawings, like reference numerals are to depict like parts, components and assemblies.

DETAILED DESCRIPTION OF PREFERRED EMBODIMENTS

The invention is based, firstly, on the finding that certain technical-physical parameters, which are required for the stimulation of nerve and muscle tissue, can be reduced significantly for inductive stimulation if the temporal course of the electric field induced in the body and the resulting currents are adapted to the dynamic behavior of ion transport processes in the nerve cell membrane. These parameters can be, for example, the required field energy, the coil loss energy, the required electric coil current, the required coil voltage, the maximum steepness of the coil voltage or the coil current, or the acoustic artifact of the coil. It is therefore advantageous to have the respective inductive stimulation devices provide different temporal course models of the current and the voltage during the pulse delivery in order to thus be able to meet the conditions for various optimization criteria.

Figure 1:
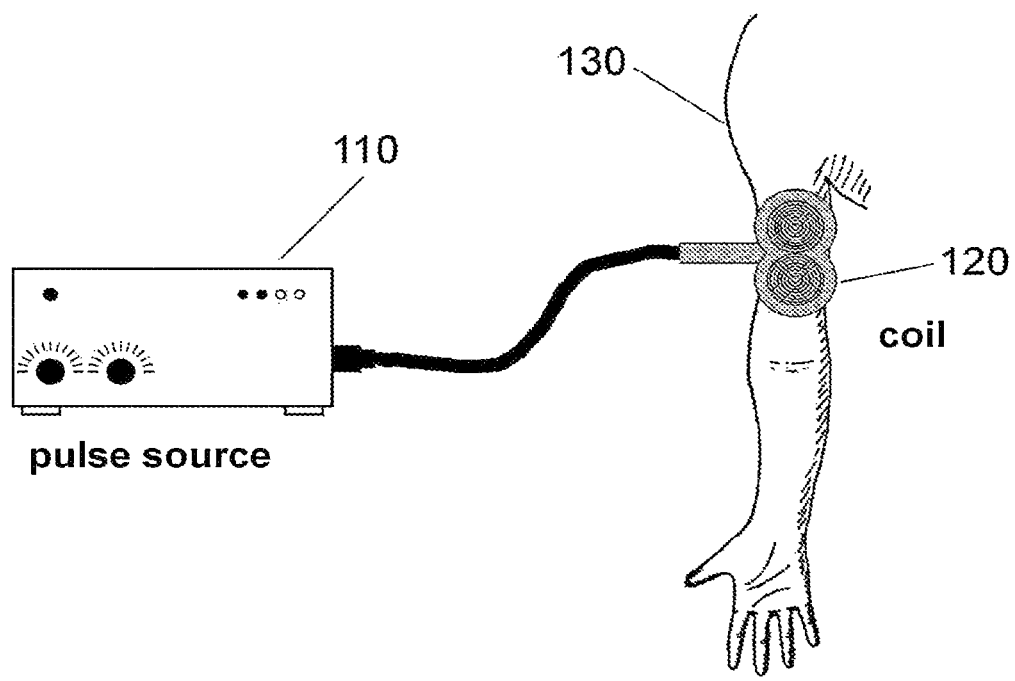
FIG. 1 shows a pulse source, the coil coupled via a cable, and the tissue structure to be stimulated (human upper arm)
Figure 2:
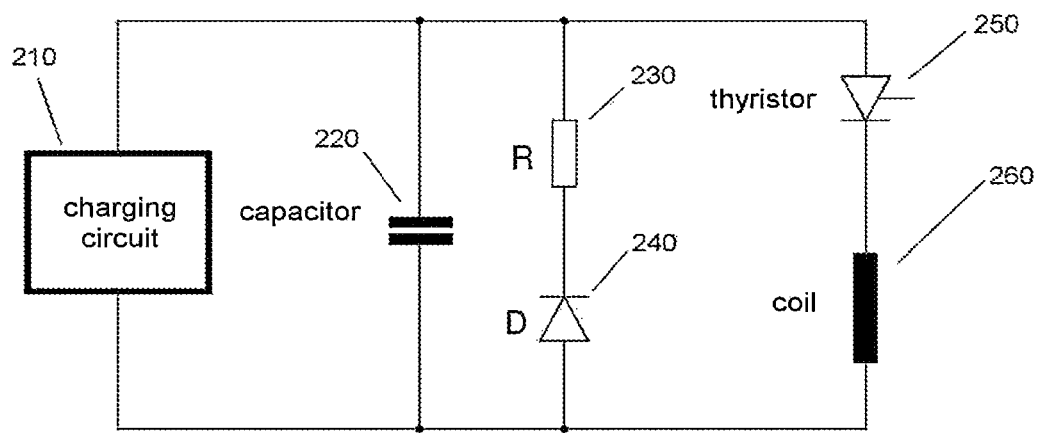
FIG. 2 shows the basic structure of a monophasic power circuit.
Figure 3:
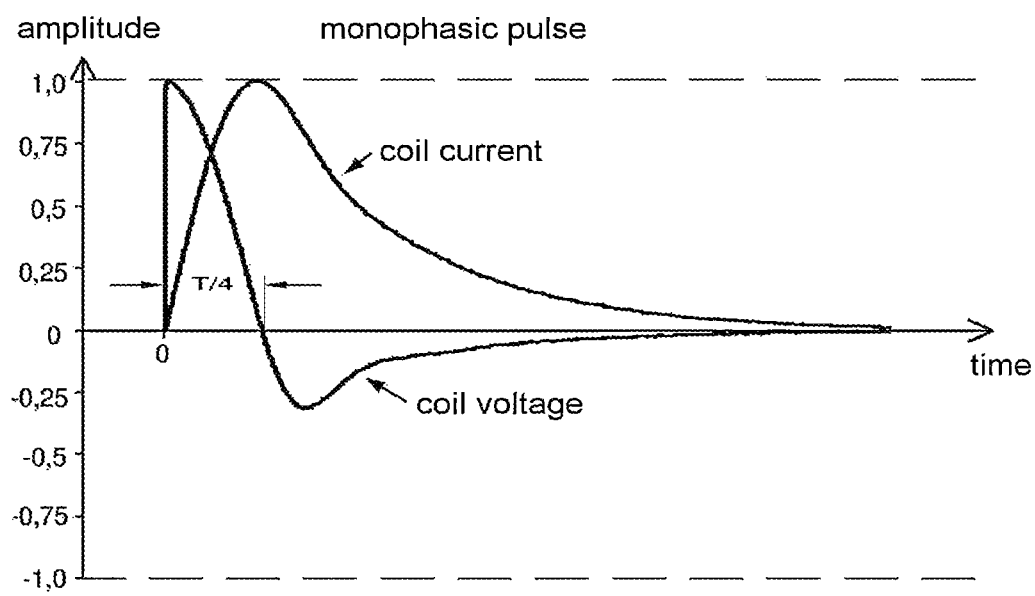
FIG. 3 shows the voltage and current curve in the coil of a monophasic stimulator during a pulse.
Figure 4:
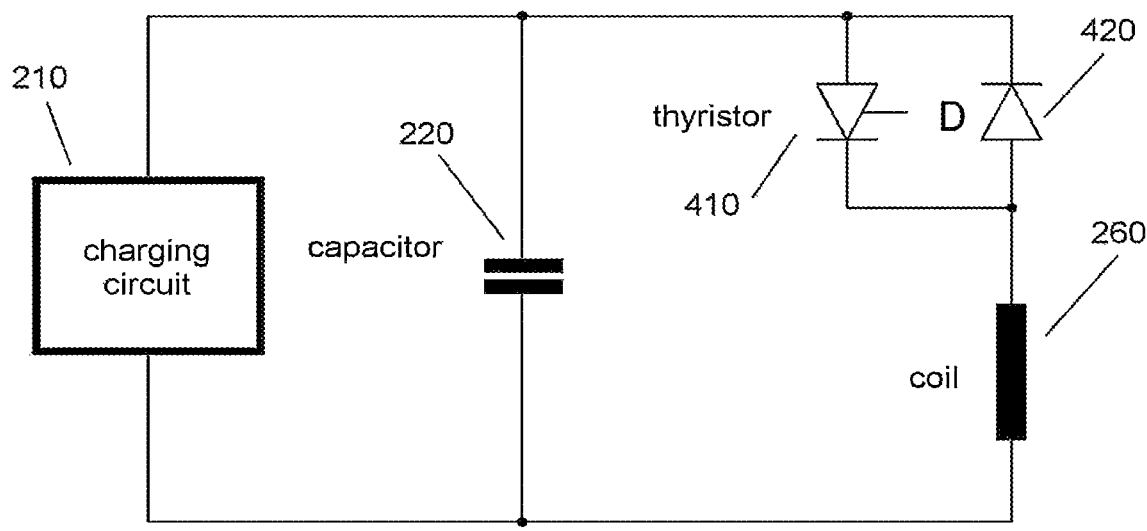
FIG. 4 shows the basic structure of a power circuit for generating sine full-waves.
Figure 5:
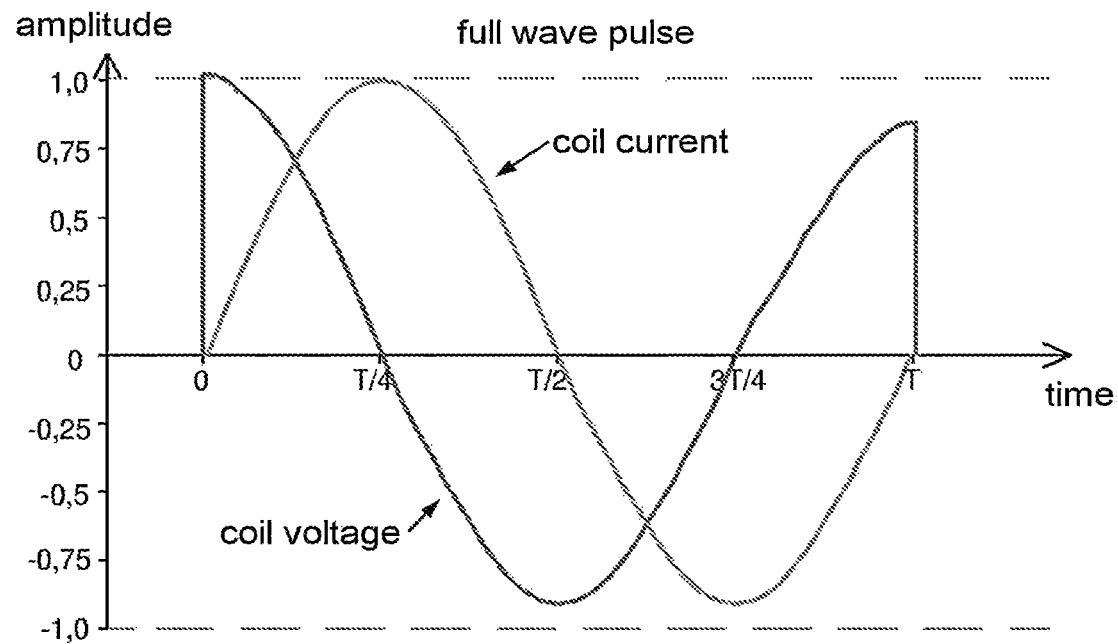
FIG. 5 shows the voltage and current curve of a full-wave stimulator in the coil during a pulse.
Figure 6:
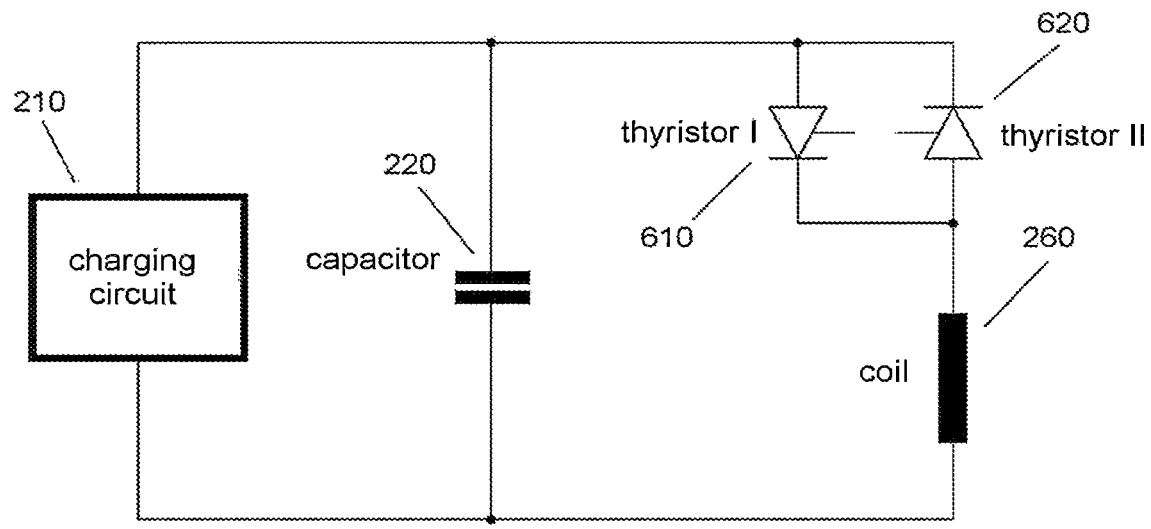
FIG. 6 shows the basic structure of a power circuit for generating sine half-waves.
Figure 7:
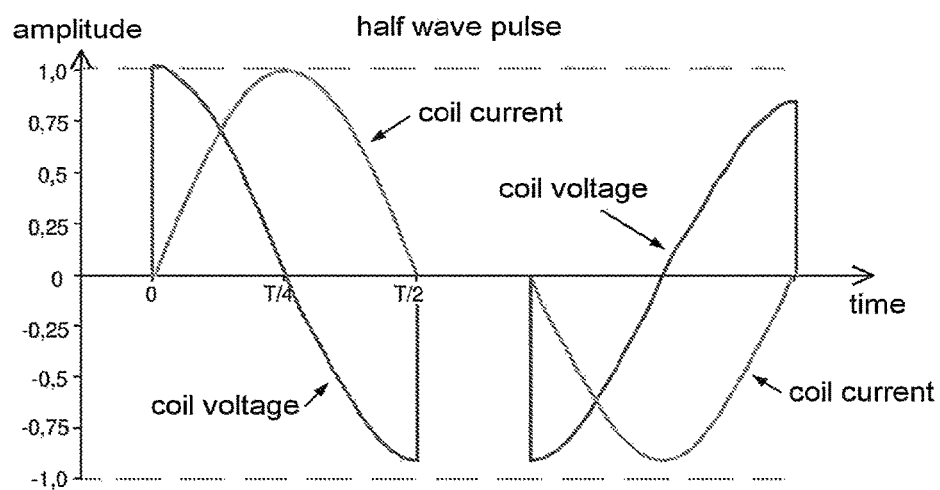
FIG. 7 shows the voltage curve and current curve of a half-wave stimulator in the coil during a pulse.
Figure 8:
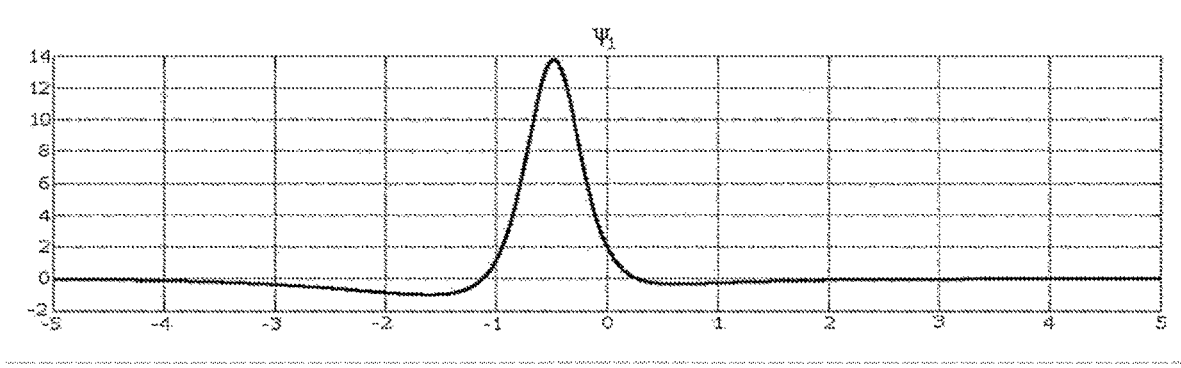
FIG. 8 shows by way of example an optimized temporal course of the necessary current at a cell membrane (and thereby also the curve of the coil voltage) during a stimulation pulse, as it is obtained as the optimized result of nerve cell modeling.

FIG. 8 shows by way of example a very favorable temporal course of the current for the excitation of a nerve cell that makes it possible to trigger an action potential in axons having a low amplitude or stimulus energy. In particular, the first negative partial oscillation with a low amplitude—visible in FIG. 8—prior to the actual positive stimulation pulse, can significantly reduce the amplitude of the required current necessary for the stimulation due to its excitation of dynamic processes at the membrane level. This means for example, that when the associated power electronics generates a temporal course of the pulse such that the coil voltage and thereby also the electric field induced in the body have a profile, as is shown in FIG. 8, then the required stimulus energy can be reduced. As a result, the respective pulse source can be significantly reduced in size and produced at lower costs. A further advantage is that the coil losses can be significantly reduced, so that series of pulses can be delivered in short sequence (so-called repetitive stimulation) over significantly longer periods of time.

The finding regarding the necessary temporal course profiles of the field can be based, for example, on the mathematical modeling of nerve cells, as it was first established by Hodgkin and Huxley (A. L. Hodgkin, A. F. Huxley: "A Quantitative Description of Membrane Current and its Application to Conduction and Excitation in Nerve". "Journal of Physiology", 117, 1952, p. 500-544). Such a model is based on a set of non-linear differential equations and simulates the electric behavior of nerve cells, in particular the behavior of short membrane segments of axons. With this model, for example, the reaction of an axon to electrical currents acting from outside can be demonstrated. Therefore, the required stimulation currents can be computationally determined for various temporal courses of the pulses that are required to trigger an action potential in the nerve cell. However, such an approach also suggests that a pulse-width modulated voltage source, which is typically used as a power converter in energy technology, is by no means suited to create such a desired temporal course for the electric field strength in the tissue. The reason for this is that pulse-width modulated actuation of the coil in the body tissue would lead to an electric field profile with an almost identical (also pulse-width modulated) profile. Due to the high field strength peaks, however, such a profile would develop a completely different effect than a continuous or finely stepped temporal course.

Furthermore, the invention is based on the realization that such a pulse source of high power with simultaneously low losses can be set up with a series connection of controlled two-terminal circuits, where the two-terminal circuits each contain electrical energy storage elements, such as capacitors, and where the voltages of these energy storage elements must be matched in a specific manner. The two-terminal circuits are configured as four-quadrant modules and can connect the respective energy storage elements to their two terminals either directly or inverted. Furthermore, the four-quadrant modules can also assume a so-called bypass state in which a direct electrical current path is switched between the two terminals, but the energy storage element is at the same time neither charged nor discharged. Each four-quadrant module of such a series connection then provides a positive or negative voltage component according to the voltage of its energy storage element, or it only switches through the corresponding current path between its terminals and does not contribute to the total voltage.

This pulse source can consist in particular of one (or several) supplied main module (connected in series) which in turn is disposed in series with at least one of the four-quadrant modules mentioned. The respective energy storage element of the main module is charged by a voltage source, in particular prior to delivering the pulse. The energy storage element of the main module preferably stores the electrical energy for the generation of the pulse (for example in the stimulation coil). The comparatively high electrical power, which is exchanged with the stimulation coil during the pulse, can then be made available via the energy storage element of the main module, without the corresponding power supply needing to make a significant contribution. The energy storage elements of the four-quadrant modules can preferably have a significantly lower energy content, since they can be charged and discharged via the series connection of all modules during the pulse delivery. Furthermore, the energy storage elements of the four-quadrant modules can also be charged by a respective power supply before the pulse is delivered.

Both the main module as well as the four-quadrant modules represents electrical two-terminal circuits which are connected in series according to one aspect of the invention. The two ends of this series connection therefore form the output of the pulse source and are connected accordingly to the stimulation coil. Such a circuit is therefore able to output almost any finely stepped temporal course of a voltage.

Typical stimulation pulses for the stimulation of human axons have a pulse duration of 50-300 µs. With repetitive stimulation, pulses are output at a repeat rate of 30-100 Hz. Recharging the energy storage element of the main module with comparatively small power is therefore possible during the pauses between two pulses.

The four-quadrant modules connected in series can be structured like modules 930, 940 shown in FIG. 9. They are referred to as four-quadrant modules because both the current as well as the voltage at the two terminals 910, 911 can be arbitrarily positive or negative. Instead of transistors 901 to 904 shown, other electrically switching components can also be used. Two of transistors 901 and 902 or 903 and 904, respectively, connected in series each form a so-called half bridge. A diode 905 to 908 is connected parallel to these transistors and can also be the integrated body diode of the respective transistors. In principle, any kind of actuateable switch can be used for the switching elements. Accordingly, full bridge 940 can also be realized by four switches. The transistors or switches can electrically connect output terminals 910 and 911 to capacitor 909. These individual modules can, in particular, be switched by way of their switches to the following four states:

predetermining a positive terminal voltage with respect to two terminals 910 and 911 for any current direction; obtainable by simultaneously switching transistor switches 901 and 904;

predetermining a negative terminal voltage with respect to two terminals 910 and 911 for any current direction; obtainable by simultaneously switching transistor switches 902 and 903;

bypass state (i.e. no energy take-up or delivery by the individual module), free current flow in any direction; obtainable by simultaneously switching transistor switches 901 and 903 or transistor switches 902 and 904;

forcing energy take-up by the individual module by imposing the voltage level; for example, if all transistor switches are cut off and the magnitude of the terminal voltage applied from the outside exceeds the voltage of the capacitor.

The main module of the pulse source can either be structured like a four-quadrant module, where it additionally requires an electrical power supply to charge the capacitor. Furthermore, several such main modules with their respective energy storage elements can be connected in series. Alternatively, the main module can also be configured as a two-quadrant module, so that it can only deliver positive voltages for any current direction.

The essential switching states of such a two-quadrant module are: delivering the full voltage of the energy storage element or bypass state. FIG. 9 shows such a module 950 which consists of two switches, 923, 924 and a capacitor 929 as the energy storage element. The voltage is output via terminals 920, 921. However, when using a two-quadrant module as the main module, the range of voltage that the pulse source can deliver during the course of the pulse is more limited than when using a four-quadrant module.

All switching elements of the modules can be configured, for example, as transistors (for example, MOSFET or also IGBT) or other semiconductor switches and improved in terms of current carrying capacity by parallelization.

Figure 10A:
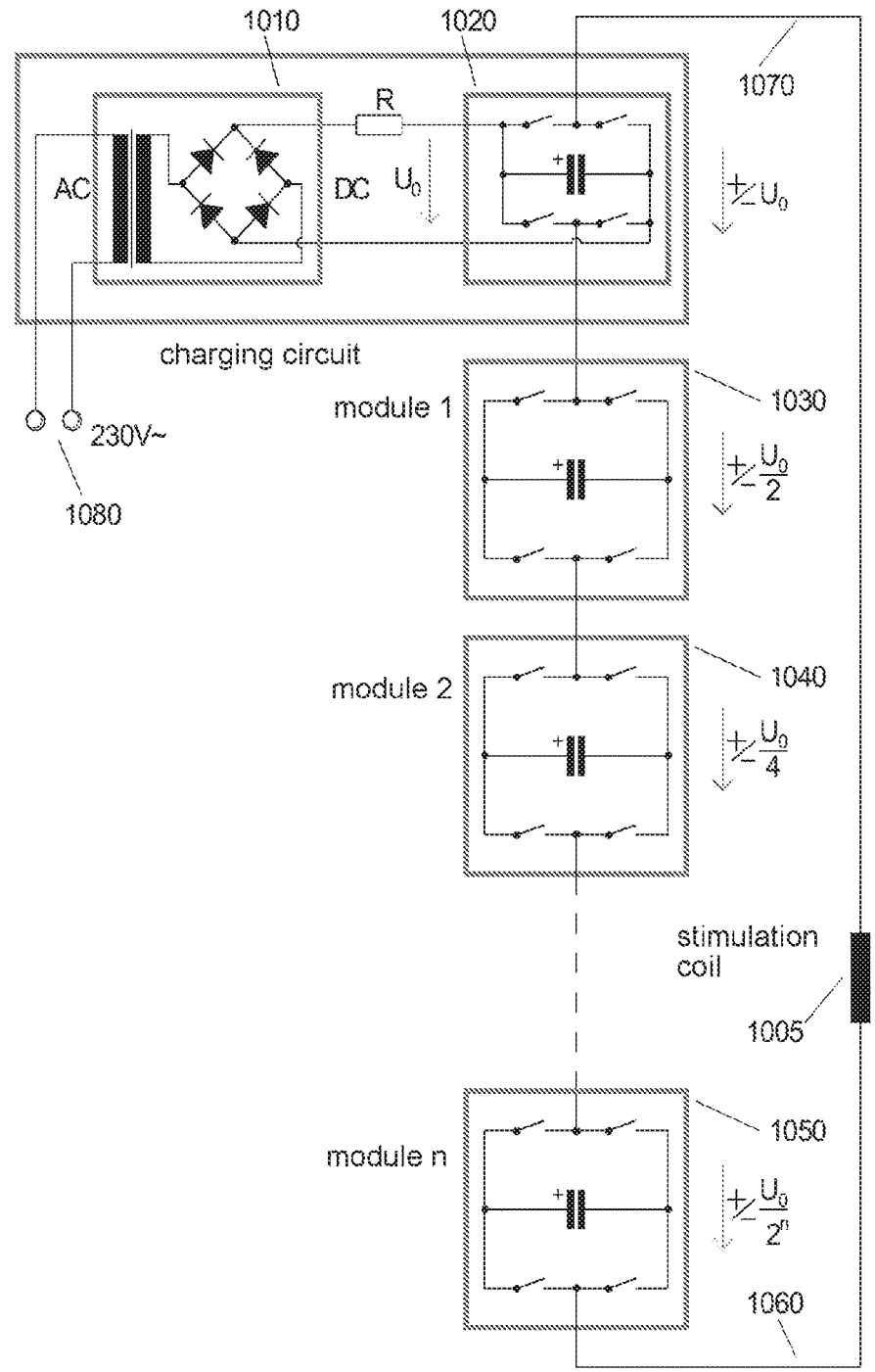
FIGS. 10 a,b show the principal structure of a pulse source, according to preferred embodiments of the invention, each consisting of a module to be charged and a chain of four-quadrant modules.

FIG. 10*a* shows the circuit of a possible embodiment of the pulse source. A charging circuit 1010 is directly connected to the main module 1020. Disposed in series therewith are n four-quadrant modules 1030, 1040, 1050, where n can be any integer greater than or equal to 1. The voltages of the energy storage elements can preferably be stepped down according to the powers of two. The more four-quadrant modules are used for the pulse source (i.e. the larger n), the more voltage levels can be set. Stimulation coil 1005 is connected directly to the two output terminals 1060, 1070 of the pulse source. The supplied main module contains an energy storage element whose capacity is preferably large enough to deliver the required energy of the pulse. This energy storage element is charged by a charging circuit 1010 prior to pulse delivery. The charging power can be small compared to the electrical power of the pulse, so that the charging process of this energy storage element may take considerably longer than the pulse itself. The supplied main module can also be a four-quadrant module—as shown in FIG. 10. Alternatively, a two-quadrant module 950 according to FIG. 9 can be used there. Furthermore, the energy storage elements of the n four-quadrant modules can likewise be precharged by a charging circuit before the pulse is delivered. This process requires comparatively very little energy, since the capacities of the n four-quadrant modules are preferably much smaller than the capacity of the main module.

In addition, instead of the embodiments shown, alternative circuit topologies can be used for the main module, the essential property of which is to optionally connect an energy storage device directly to a subsequent chain of four-quadrant modules 1030, 1040, 1050 or establish a bypass of the chain of four-quadrant modules directly to an output terminal 1060. The charging circuit can be directly connected, for example, to the power grid by way of its terminals 1080. During pulse delivery, the energy storage elements of the four-quadrant modules can be recharged by appropriately connecting directly or inverted into the current path.

Stimulation coil 1005 for nerve stimulation is connected directly to the two output terminals 1060, 1070 of the pulse source. By selecting the switching states of each individual four-quadrant module 1030, 1040, 1050 and supplied main module 1020, a desired instantaneous value of the voltage can be set at the output terminals of the pulse source. Due to a fast temporal sequence of such instantaneous values set, the pulse source can therefore represent a desired temporal course of the output voltage in fine steps. The voltage of the energy storage element of the supplied main module is preferably higher than the voltages of the energy storage elements of the four-quadrant modules; furthermore, the voltages of the energy storage elements of all modules are stepped down among each other, for example to the powers to two, as shown in FIG. 10*a*, where the main module represents the highest voltage step. The energy storage elements—except for the energy storage element of the main module—can each be charged or discharged during the pulse by polarity reversal processes, so that their respective voltage can be controlled within small limits. These polarity reversal processes can be triggered by the respective switching states. The current, which then respectively charges or discharges the energy storage elements, corresponds to the current flowing through the entire series connection of modules and the stimulation coil. This current can change its polarity during the delivery of a pulse according to the inductance of the coil.

During the delivery of a pulse the voltage of the energy storage element of the supplied main module can change due to the energy consumption in the coil voltage circuit. Accordingly, the voltages of the individual energy storage elements of the four-quadrant modules are preferably also adapted to the changed voltage of the energy storage element of the main module, in order to thus maintain the desired step-down of the individual voltages.

Figure 10B:
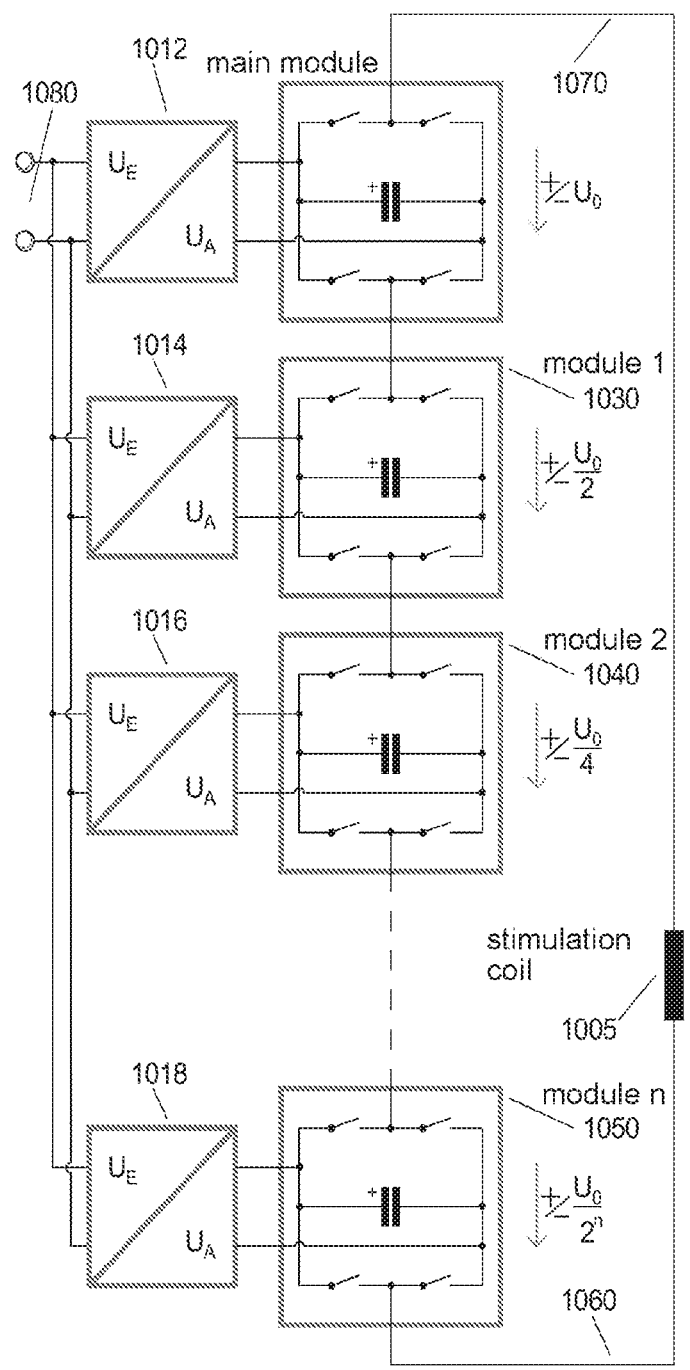

FIG. 10*b* shows a further embodiment of the pulse source, in which the energy storage elements of all modules are charged by respective voltage sources 1012, 1014, 1016, 1018 (presently shown as isolated DC-DC converters) prior to the delivery of the pulse. The circuits of the modules and the power circuit are there identical to those of FIG. 10*a*.

The individual switches of the modules are controlled by a respective controller or controller device. This controller can detect the instantaneous voltage or states of charge of the energy storage elements of the modules by measuring. Alternatively, the controller can also calculate in advance and thereby indirectly detect the expected states of charge of the energy storage elements during pulse delivery by way of a simulation of the course of the pulse. The voltages of the energy storage elements can then be determined indirectly and the required switching states of the modules during the pulse can thus be determined.

Figure 11:
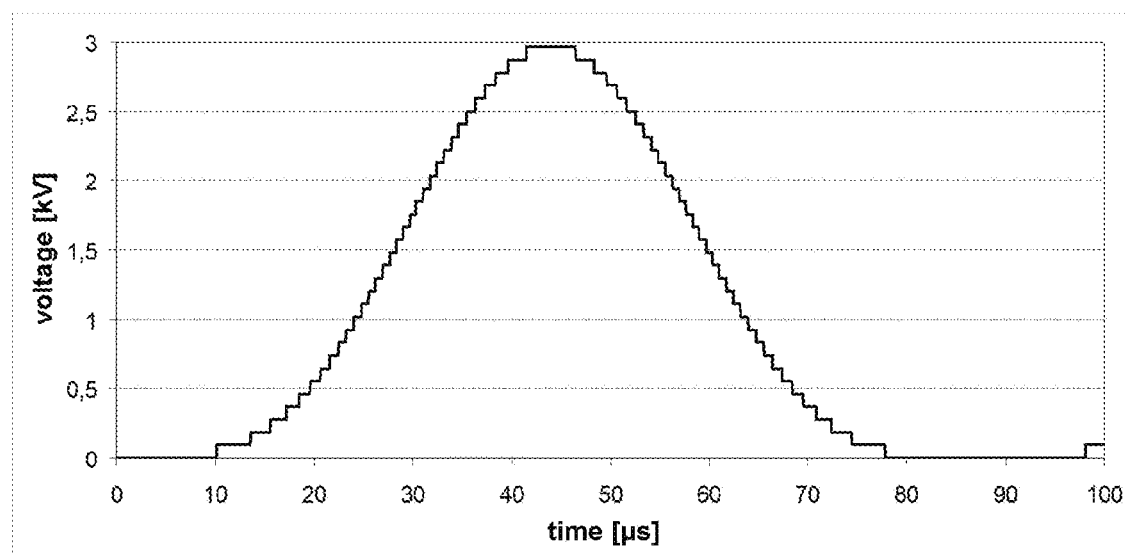
FIG. 11 shows the approximation of a desired temporal course of the voltage of a stimulation pulse by correspondingly fine steps, as they can be created according to the invention.

FIG. 11 shows as an example the finely stepped voltage curve of a stimulation pulse, as it could be delivered from a pulse source according to the invention to a stimulation coil for inductive nerve stimulation. The voltage curve shown in this example exhibits only positive voltage values. For outputting such a voltage curve, it is sufficient if the supplied main module of the pulse source can also generate only positive voltages. In this case, it is therefore sufficient if the supplied main module is configured as a two-quadrant module. In the present case, the voltage curve shown is represented by 32 steps. This requires a main module and 7 four-quadrant modules.

By adding an additional (e.g. in-phase) analog module to the series connection of modules, the pulse source can also be modified such that it can generate continuous output voltages instead of a stepped voltage curve. The voltage stroke of such an analog module must be only marginally greater than the voltage value of the module with the smallest voltage. Such comparatively small voltages can be controlled in-phase relatively easily by power transistors, even for high currents. In contrast, generating such a high-energy pulse, as is required for magnetic stimulation, by purely in-phase control would be technically extremely complex, since extremely large power would there need to be controlled by corresponding transistors and switching transistors in parallel at high performances and voltages is hardly possible.

Alternatively, filter circuits can be used to smooth the voltage levels.

Examining a Module Chain

Figure 12:
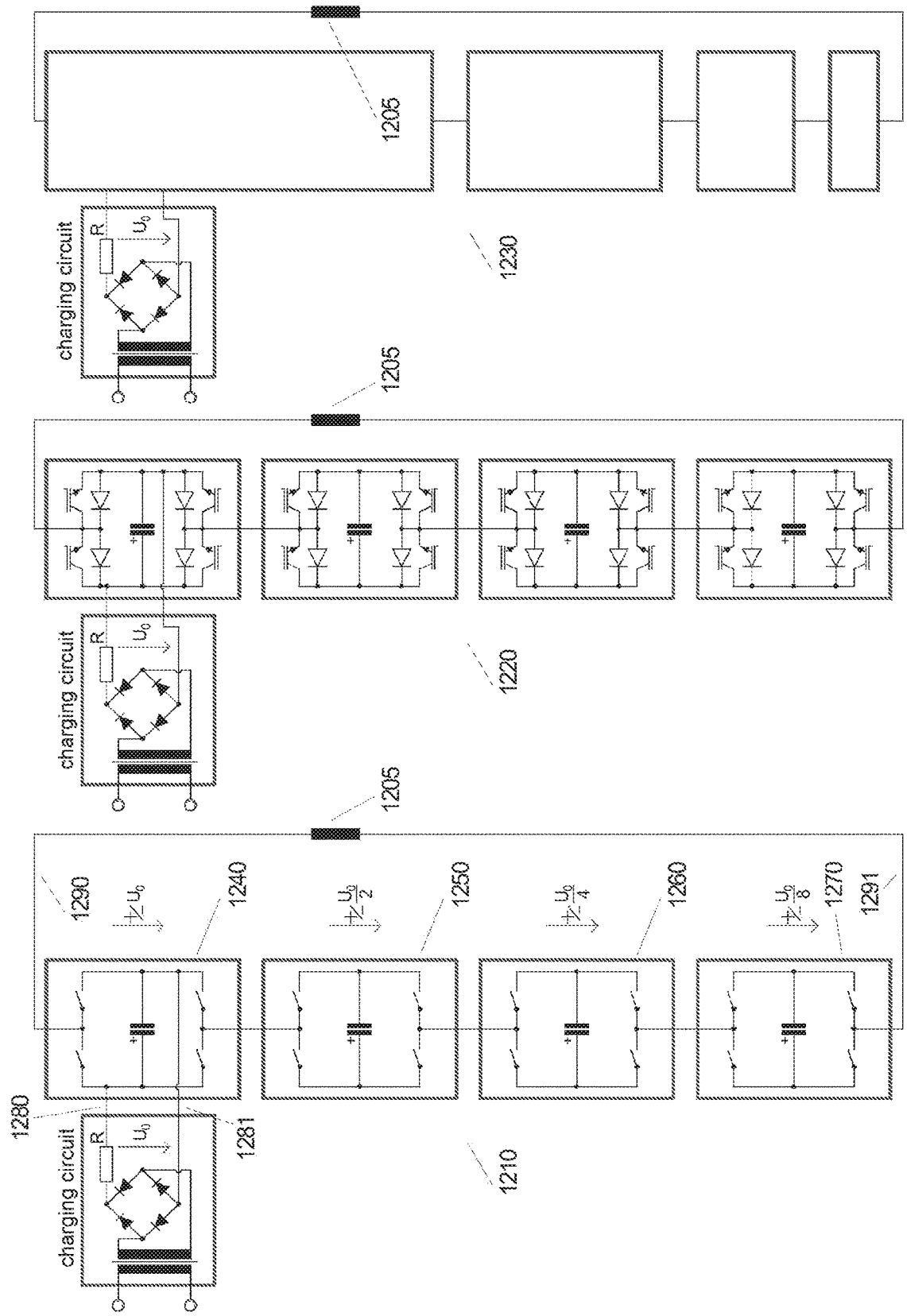
FIG. 12 shows a pulse source circuit according to the invention, consisting of 4 modules in three modes of representation.

[paragraph 84] FIG. 12 shows such a system consisting of four modules, each of which is configured as a four-quadrant module. Where 1210 shows a circuit that can serve as a pulse source, consisting of four modules 1240, 1250, 1260, 1270, where each module is symbolically illustrated having four switches. Module 1240 represents the supplied main module. The modules following downwardly are all embodied according to the same scheme as passive four-quadrant modules with one storage capacitor each, where the voltages of modules 1250, 1260, 1270 are each halved. For the four modules shown (one supplied main module and three passive capacitor modules), the individual voltages are divided according to the values $U_0$, $U_0/2$, $U_0/4$, $U_0/8$. The output voltage delivered to stimulation coil 1205 can therefore be represented as stepped in increments of eighths relative to the maximum voltage $U_0$. This sequence of the modules is sorted strictly according to declining voltages in FIG. 12, but can be selected at random due to the series connection. Terminal pair 1280, 1281 represents the connections of the supply of the energy storage of the main module. Output terminals 1290, 1291 form the output circuit to which stimulation coil 1205 is connected. During pulse delivery, a variably stepped positive or negative voltage in the range of at least $-U_0$ and $U_0$ can be realized there. Module chain 1220 represents the pulse source with transistors and the associated body diodes; module chain 1230 shows the same modules symbolically having a length corresponding to their respective voltage.

The capacitors of the modules are discharged or charged by a respective current in the circuit of the output terminals and stimulation coil 1205 depending on the polarity switched, which leads to a corresponding rise or drop of the voltages of the capacitors. Therefore, a module whose capacitor has, for example, discharged too far (i.e. whose voltage is by a small tolerance limit below a respective target value) is switched in a next step such that its capacitor is disposed reversed in the current path. In this way, the respective capacitor is recharged by the load current. Since this reversal not only changes the terminal voltage of this module but also the total voltage of the entire chain, a different combination of modules must then be switched at output terminals 1290, 1291 according to the desired target voltage in order to obtain the same voltage value.

Figure 13:
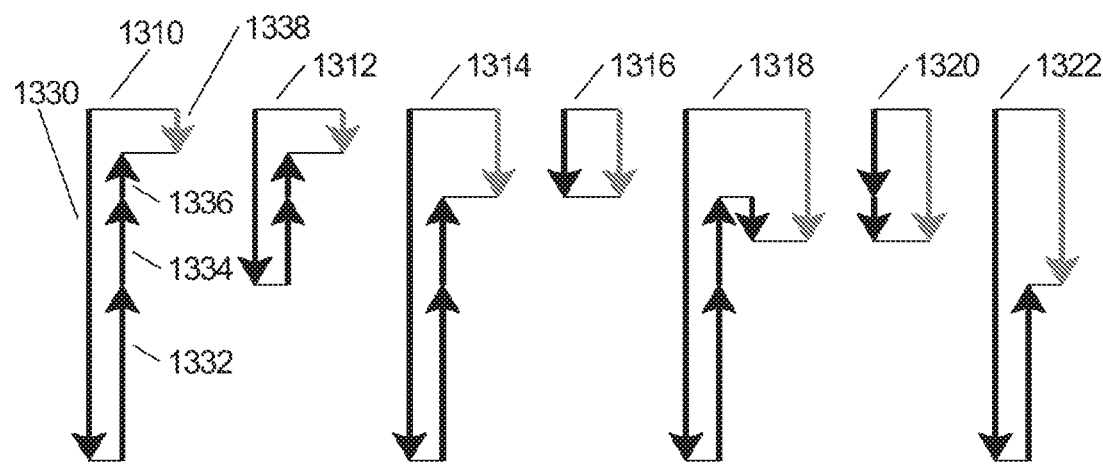
FIG. 13 shows possible voltages of activated modules and the associated output voltages for the pulse source circuit, consisting of 4 modules according to FIG. 12.

Instead of a single actively supplied main module or voltage source, respectively, several such actively supplied main modules can also be connected in series for setting up the respective pulse source FIG. 13 exemplifies a possible switching combination of the four modules according to FIG. 12 in the form of voltage arrows. The arrow length in this representation is selected proportional to the respective voltage. The black arrows symbolize the voltages of the modules currently switched active; the grey arrow corresponds to the output voltage of the system. Arrow 1330 of switching combination 1310 represents voltage $U_0$ of the supplied main module. Though modules 1250, 1260, 1270 are all switched active, they exhibit an inverse polarity. Accordingly, arrows 1332, 1334 and 1336 are shown in the opposite direction.

The directions of the arrows at the same time allow for a conclusion regarding the direction of current flow. If a load is connected to the output terminals, a downwardly direction of the arrow would correspond to current output and an upwardly direction of the arrow to current take-up. In the present case, supplied main module 1240 is discharged, whereas modules 1250, 1260, 1270 are charged. The resulting voltage, which can be tapped at terminal pair 1290, 69, is represented by arrow 1338. Accordingly, the voltage at the output terminals is positive and has a value of $U_0/8$. With switching combination 1312, the same output voltage of $U_0/8$ as in the first configuration is generated. However, the presently supplied main module is now operated in bypass, so that it does not deliver any voltage. Module 1250 would presently now be discharged, whereas modules 1260 and 1270 continue to be charged. Accordingly, there are also switching combinations, presently not shown, in which modules 1260 and 1270 can be discharged. Switching combinations 1314 and 1316 each generate voltages of $U_0/4$ and switching combinations 1318 and 1320 voltages of $3/8\ U_0$. A voltage of $U_0/2$ can be generated at the output terminals by switching combination 1322. When all arrow directions are reversed, respective negative voltages can be generated.

For a module chain, consisting of a main module which can supply voltage $U_0$ and further n−1 four-quadrant modules (i.e. a total of n modules), where the module voltages are stepped down to the powers of two, the following relationship can be shown:

Any voltage from $-U_0$ to $U_0$ can be realized in steps of $U_0/(2^{(n-1)})$ at the output terminals of such a module chain, regardless of the instantaneous state of charge of the individual energy storage elements. State of charge presently means that the respective energy storage system for each module is either in a state that it should be charged (instantaneous voltage is below the target voltage for this module) or in a state that it should be discharged (instantaneous voltage is above or equal to the target voltage for this module). For example, since, when using capacitors as energy storage elements, the voltage continuously changes when charging or discharging, constantly switching back and forth between certain module configurations must occur—according to the states of charge of the module capacitors—in order to maintain a certain voltage under load for a longer period of time (i.e. during the period of time during which a particular voltage level is to be realized in the course of the pulse). These specific module configurations each provide the same total voltages, but allow the respective module capacitors to be charged or discharged as desired. For each realizable voltage—except for 0V and the maximum voltage $U_O$—there are therefore always at least two module configurations for realizing this voltage.

This condition can also be fulfilled for other voltage steps of individual module capacitors. In particular, if multiple direct voltage circuits are available, configurations that employ multiple supplied main modules can also be used. However, it should still be taken into account that the capacitor of the main module also discharges slowly during pulse delivery, as it is not (or only slightly) recharged during pulse delivery. This also changes its voltage $U_O$. Accordingly, the capacitor voltages of the other four-quadrant modules should also be changed during the course of the pulse, so that the voltage ratios described above are upheld. Such an adjustment of the capacitor voltages can achieve respective control of the pulse source by selectively charging and discharging the module capacitors during pulse delivery—while at the same time complying with the target voltage curve.

The frequency at which such module configurations must be switched is determined, firstly, by the fineness of the permitted tolerance with regard to the module capacitor voltages, by the load current, and by the capacity of the capacitors. In particular, smaller switching frequencies can be obtained by large capacities of the module capacitors. If the module capacitors have sufficient capacities in relation to the coil current, then the module configurations do not have to be switched over during the individual voltage steps of the course of the pulse.

Conversely, the capacities of the capacitors of the four-quadrant modules—which are an important cost factor in such power electronic circuits—can be greatly reduced, in that the above process is performed with a relatively high switching frequency. However, an increase in the switching frequency increases the switching losses of the transistors.

Number of adjustable voltage steps:

In the following, the number of possible adjustable voltage steps shall be examined, starting out from stepping down the voltages of the individual energy storage elements by the powers of two. For reasons of rechageability of the four-quadrant modules, the highest voltage level is presently not the sum voltage of all n modules, but only the level of the main module. This can also be represented in binary notation, in which each module represents a binary digit, where 1 represents a positive state of charge and 0 a bypass state (the inverted state of charge can be neglected for this consideration because it is only needed for negative voltages or for recharging the modules). For a pulse source consisting of 5 modules, i.e. n=5, this highest voltage step in binary notation would be 10000 (i.e. the main module is active, the remaining 4 four-quadrant modules are in the bypass state).

This results in the number S+ of positive steps:

$$S_+ = 2^{n-1} + 1$$

This is the number of possibilities without the highest step and "+1" by the highest step. According to the representation following the binary system, zero is then already included. If one wanted to also take into account the number of possible negative steps S−, one would then have to omit step 0 accordingly, so that a total number S of obtainable voltage steps results in:

$$S = S_+ S_- = (2^{n-1}+1) + 2^{n-1} = 2 \cdot 2^{n-1} + 1 = 2^n + 1$$

SIMPLE EXAMPLES OF THE OPERATING PRINCIPLE

Example 1, Generating a Specific Voltage Level with 2 Modules

Figure 14:
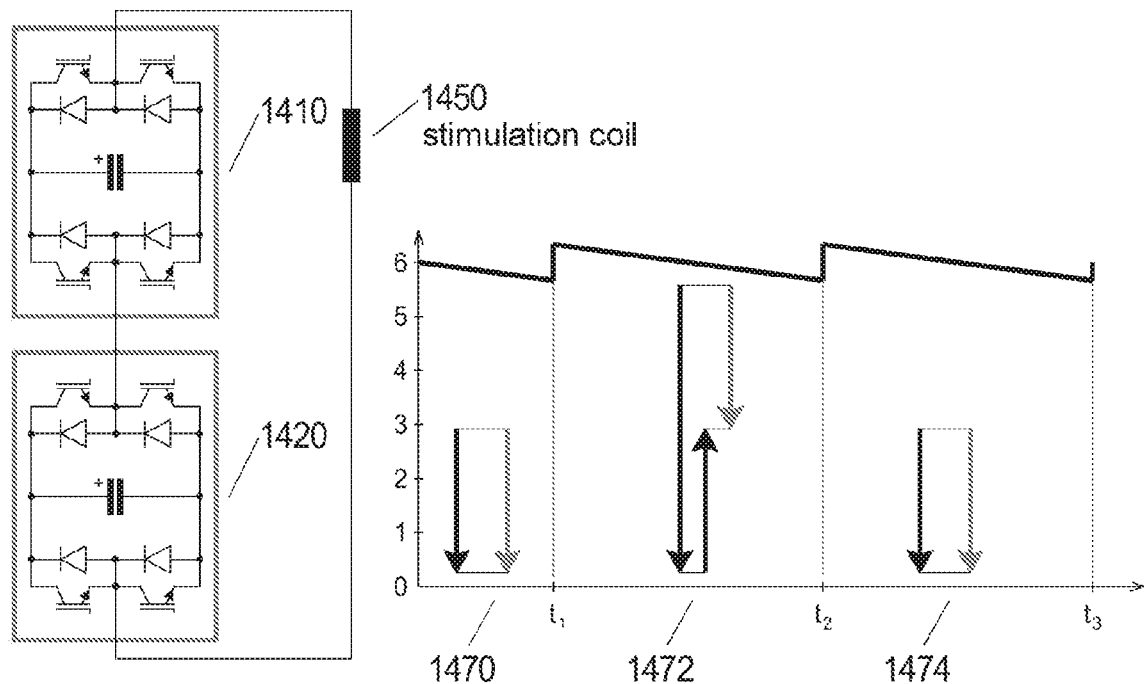
FIG. 14 shows a pulse source circuit with a total of two modules for generation and the temporal course of a voltage step set.

The pulse source circuit shown in FIG. 14 is initially to consist of only two modules, a main module 1410 with 1200V and a four-quadrant module 1420, which is to be operated at a voltage of 600V. Furthermore, the connection is first to supply to its connected stimulation coil 1450 a momentary voltage value of 600 V (i.e. the voltage of the "smallest step") whereby also a certain coil current is to flow. The initial configuration is chosen in such a way that the 600V module is precharged with 600V.

Period 0 to $t_1$, 1470:

The 1200V module is first switched to the bypass state (e.g. in which only the two transistors of this module on the right-hand side are switched on).

The 600V module delivers the demanded 600V, where the module capacitor, however, discharges over time until a lower tolerance threshold has been reached. For example, if the voltage is below 590 V, the system must then switch over.

Period t1 to $t_2$, 1472:

Now the 1200V module is switched active to +1200V, while the 600V module with its reduced voltage of 590V is switched negative in series. This now results in a new total voltage of 1200V−590V=610V, which—this time due to the capacitor being charged—slowly drops to the tolerance threshold again. The total capacity of the series connection of two modules is slightly reduced in comparison to the first period, since the capacity of the main module is preferably significantly larger than that of the four-quadrant module (it is assumed here in a simplifying manner that the capacitor voltage of the 1200V module does not change during the short pulse). Due to the inverted operation, the 600V module is charged to a voltage of 610V. At the same time, the voltage of the main module may drop slightly, as already discussed above.

Period $t_2$ to $t_3$, 1474:

Here again, only the 600V module is positively active so that the third period is as long as the second one.

Example 2, Generating Direct Voltage with 3 Modules

Figure 15:
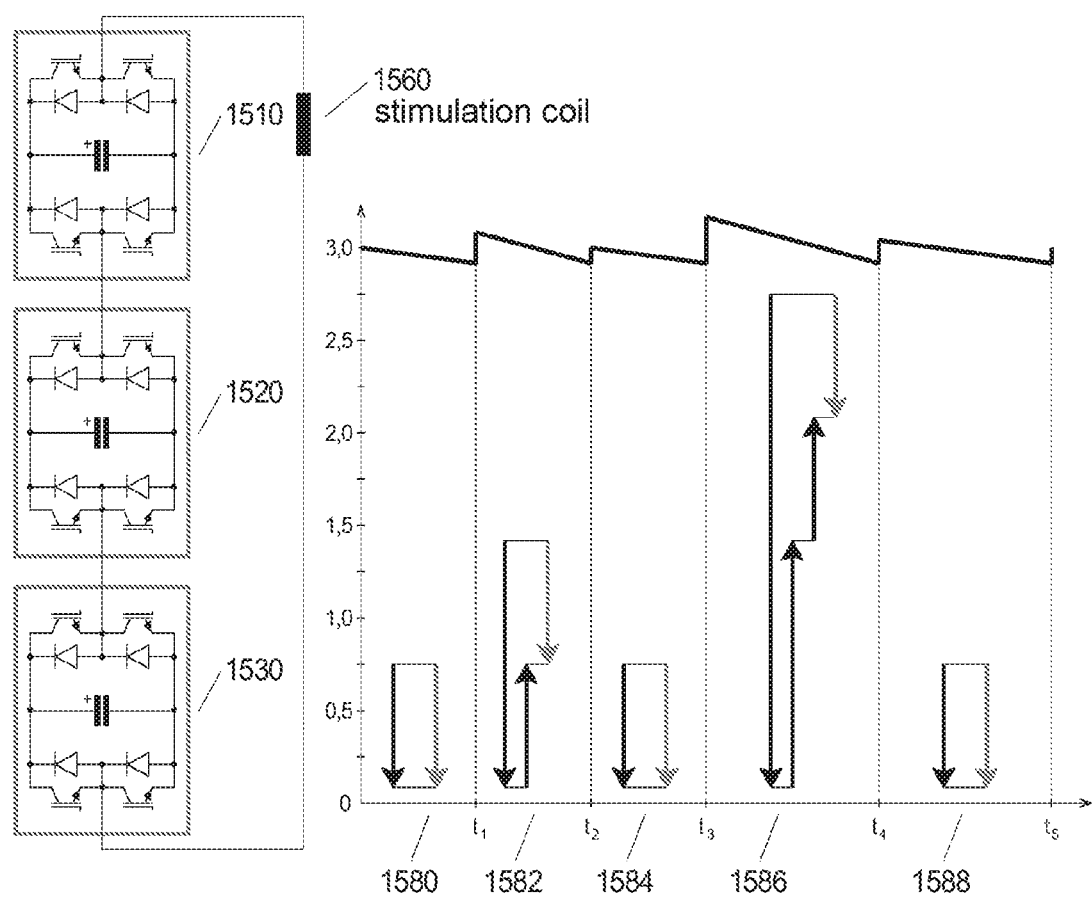
FIG. 15 shows a pulse source circuit with a total of three modules for generation and the temporal course of a voltage step set.

The pulse source circuit shown in FIG. 15 is initially to consist of three modules, a main module 1510 with 1200V and two four-quadrant modules 1520, 1530, one module for 600V and one module for 300V. Here as well, it is again to be assumed that the capacity of the main module capacitor is so large that its voltage does not change during the short pulse output, or only slightly. The circuit is now to supply an instantaneous voltage value of 300V to stimulation coil 1560, where a coil current again flows as load current. The initial configuration of the power converter is there again chosen in such a way that the 600V module is precharged with 600V and the 300V module with 300V.

Period 0 to $t_1$, 1580:

The 1200V module and the 600V module are initially switched to the bypass state. The 300V module delivers the required 300V, where the module capacitor, however, discharges over time until a lower tolerance threshold of, for example, 290V has been reached.

Period $t_1$ to $t_2$, 1582:

The 600V module is now activated and the 300V module is connected in series reversed. The initial voltage there is now 600V−290V=310V. This process continues until the total voltage has again dropped to 290V, due to the load current of the coil. At this point in time (assuming the same capacity of the module capacitors), the voltage of the 300V module has again risen to 300V; the voltage of the 600V module is now 590V. The voltage difference passed through is twice as high as in the first period; however, two module capacitors (e.g. of the same capacity) are now disposed in series, so that the time span is equally long as the first one.

Period $t_2$ to $t_3$, 1584:

Since the 300V capacitor has now been charged to 300V again, a cycle like in the first period can be used again. At the end of this period, the 300V module capacitor is discharged accordingly to 290V.

Period $t_3$ to $t_4$, 1586:

Now both the capacitor of the 300V module as well as that of the 600V module are discharged below the respective tolerance threshold. Therefore, these two module capacitors are switched anti-serially to the 1200V main module. This results in a starting voltage of 1200V−590V−290V=320V. Due to the two capacitors disposed in series, the voltage drops about as fast as in the second phase (again assuming that the capacity of the main module is significantly larger than that of the two four-quadrant modules); however, the voltage stroke is slightly greater, because the voltage now drops from 320V to 290V. At the end, the capacitor voltage of the 600V module according to the example is 605V and that of the 3V [sic] module is 305V.

Period $t_4$ to $t_5$, 1588:

The 300V module can now be activated alone again; the voltage drops from 305V to 290V.

According to these examples, the step function shown in FIG. 11 can be considered as a chain of short-term direct voltage values to be output. Therefore, such a voltage step can have quasi a substructure, if several charging and discharging cycles of modules are required during the period during which a voltage level is to be maintained.

Advantages of Preferably Embodiments of the Invention

The proposed pulse source allows for an almost free selection of the pulse shape for the stimulation of nerve and muscle cells. Pulses that are optimized in terms of a parameter, such as the energy demand, the maximum coil voltage or the resulting click noise of the coil can thus be generated. This in turn allows the devices to be optimized in terms of their design and application (for example, small, mobile pulse sources or coils which can apply long series of stimulations due to the reduced losses).

The free selection of the pulse shape—depending on the pulse shape—also enables specifically stimulating certain nerve cell populations, preferably while other cell types can accordingly be better shielded from undesirable stimulation. In this way, a desired destination can be stimulated even better than was possible with previous devices.

In particular, the ability to generate any number of pulse shapes as desired with a single device represents a considerable advantage over devices that are configured according to prior art described. When using these prior art devices, a separate device was required for almost every pulse shape.

Fields of Application of the Invention

On the one hand, the pulse source presented can be used for all fields of magnetic neurostimulation where prior art devices have already been used. However, the pulse sources according to the present invention in terms of their functionality combine all previous stimulation devices to a single circuit.

Accordingly, the pulse source according to the invention can be used, for example, in the fields of neurorehabilitation (e.g. muscle training, re-learning of movement patterns), neurosurgery (preoperative cortical mapping), for tinnitus treatment, accident surgery, as well as in numerous fields of neurological research.

Furthermore, new research, diagnostics and therapy applications which are specifically based on the high flexibility of the pulse shape can also be developed with the novel pulse source. For example, painlessly complex nerve examinations and nerve analyses can be carried out, which—based on a large number of different individual pulses applied and their stimulation responses—can classify different cell types or—based on a disease-related change in the electrical cell parameters—can diagnose respective neurological diseases.

Furthermore, the circuit can also be used for other applications where high-power electrical pulses with a freely selectable pulse shape are required.

The invention claimed is:

1. Pulse source for the application of induced electrical pulses in the medical field, with a modular pulse source for generating voltage pulses having a controllable temporal course, a stimulation coil connected to said modular pulse source for generating a magnetic field due to the voltage pulses acting upon the stimulation coil, for generating induced electrical pulses, and a charging circuit, said modular pulse source comprising:
at least one main module to be charged by way of said charging circuit,
n−1 further modules, where n is an integer and n≥2 is true, where all at least n modules are connected to each other in series by way of module terminals thereof,
where each of the further modules comprises an energy storage device, a capacitor for storing charge, and each module comprises switching devices, formed by transistors, for selective and controlled setting of at least one active normal operation, in which said respective module introduces a voltage at its energy storage device into a voltage path of a series connection; a bypass operation, in which said respective module only connects through the voltage path of said series connection; and an inverted operation, in which the respective module introduces the voltage at its energy storage device inverted into a serial voltage path,
a controller device for directly or indirectly detecting states of charge of said energy storage devices of all n modules and for controlling switching states of said switching devices of all n modules in order to be able to selectively set a specific operating state for each of said n modules for a certain point in time,
where said controller device is configured so that the state of charge of each energy storage element of a respective module during operation is held substantially between predetermined limit values and during the active normal operation of said respective module thus leads to a predetermined voltage contribution into the voltage path, and where voltage contributions of said modules during periods of application differ and are stepped down relative to each other according to the powers of two, and
wherein said stimulation coil is coupled to an output voltage of said series connection of said modules.

2. Pulse source according to claim 1, in which the controllable temporal course of said voltage pulses is of a nature that the electrical pulses induced by said stimulation coil trigger action potentials in nerve or muscle cells of the body tissue during the application.

3. Pulse source according to claim 2, in which said controller device controls the switching states of said switching devices in a way that the desired temporal course of the voltage pulses is additionally approximated by a pulse width modulation.

4. Pulse source according to claim 2, in which the induced electrical pulses generated by said stimulation coil exhibit an optimized temporal course, so that the energy of the magnetic field required to trigger action potentials is minimized.

5. Pulse source according to claim 1, in which said energy storage device of each module is an electrolytic capacitor or a ceramic capacitor.

6. Pulse source according to claim 1, in which said switching devices of each module are formed by MOSFETs or IGBTs.

7. Pulse source according to claim 1, in which detection of the states of charge of said energy storage devices of said modules is indirect and is respectively effected by said controller device by way of a calculation of the energies exchanged via said energy storage devices.

8. Pulse source according to claim 7, in which the calculation of the energies exchanged via said energy storage devices is effected by a simulation of the voltage pulse to be generated such that the switching states of said switching devices of all n modules are calculated in advance prior to the generation of the voltage pulse having the controllable temporal course.

9. Pulse source according to claim 1, with a downstream smoothing circuit for smoothing the output voltage of said series connection of said modules.

10. Pulse source according to claim 1, where said modules are configured as four-quadrant modules with a normal operation, a bypass operation and an inverted operation and the voltage contributions of all modules are stepped down relative to each other according to the powers of two.

11. Pulse source according to claim 1, where at least one alternative module configuration is provided for each module and the configuration of each module is predetermined by switching individual switching devices of said modules and the resulting output voltage, other than module configurations for maximum, minimum and zero output voltages, and can be set and substantially leads to the same output voltage, where switching to the alternative module configuration allows modules, which are to be recharged for maintaining their desired state of charge, to be switched to the inverted operation as part of the alternative module configuration in order for the modules to thus be recharged without altering voltage level at the output.

12. Pulse source according to claim 1, where the detection of the state of charge of each module is effected by said controller device, and this detection is effected either directly at said respective module or on the basis of the output voltage and an instantaneous switching state.

13. Method for generating induced electrical pulses for medical applications, comprising the following steps:
operating a modular pulse source, said modular pulse source comprising: at least one main module to be charged by way of a charging circuit, n−1 further modules, where n is an integer and n≥2 is true, where each modules comprises an energy storage device, a capacitor for storing charge, and each module comprises switching devices, formed by transistors, for selective and controlled setting of at least one active normal operation, in which said respective module introduces the voltage at its energy storage device into a voltage path of a series connection, and a bypass operation, in which said respective module only connects through the voltage path of said series connection, and an inverted operation, in which said respective module introduces the voltage at its energy storage device inverted into a serial voltage path,
connecting said n modules in series,
charging said storage device of said main module by way of a charging device,
predetermining a desired temporal course of the output voltage in relation to the amplitude over time,
maintaining predetermined states of charge for said individual modules during a period of application in such a way that each module in its active operating state substantially makes a predetermined voltage contribution to the series connection, where voltage contributions of said modules differ from each other and are stepped down relative to each other by the powers of two,
actuating said switching devices of said modules during the period of application to switch each module to an operating state so that the sum of individual module voltages as they are provided by said energy storage device of each module according to its active, inverted or bypass operation at all times corresponds to a predetermined range of the output voltage,
coupling an output voltage to a stimulation coil for generating a magnetic field due to voltage pulses acting upon said stimulation coil for generating induced electrical pulses.

14. Method according to claim 13, in which the temporal course of said voltage pulses is of such nature that the electrical pulses induced by said stimulation coil trigger action potentials in nerve or muscle cells of the body tissue.

15. Method according to claim 14, in which actuating said switching devices is effected such that the desired temporal course of the output voltage is additionally approximated by a pulse width modulation.

16. Method according to claim 14, in which the induced electrical pulses generated by said stimulation coil exhibit an optimized temporal course, so that the energy of the magnetic field required to trigger action potentials is minimized.

17. Method according to claim 13, in which indirect detection of the output voltages of said energy storage devices of said modules is effected by way of a calculation of the energies exchanged via said energy storage devices.

18. Method according to claim 17, in which the calculation of the energies exchanged via said energy storage devices is effected by a simulation of the desired temporal course of the output voltage such that actuating said switching devices of all n modules is calculated in advance prior to the action of a voltage pulse upon said stimulation coil.

19. Method according to claim 13, where at least one alternative module configuration is provided for each module and configuration of each module is predetermined by switching individual devices of said modules and the resulting output voltage, other than module configurations for maximum, minimum and zero output voltages, and can be set and substantially leads to the same output voltage, where switching to the alternative module configuration allows modules, which are to be recharged for maintaining their desired state of charge, to be switched to the inverted operation as part of the alternative module configuration in order for the modules to thus be recharged without altering voltage level at the output.

20. Method according to claim 13, where the detection of the state of charge of each module is effected by said controller device, and this detection is effected either directly at said respective module or on the basis of the output voltage and an instantaneous switching state.

* * * * *